US007318461B2

(12) United States Patent
Zeller

(10) Patent No.: US 7,318,461 B2
(45) Date of Patent: Jan. 15, 2008

(54) CONTAINER CARRIER FOR SAMPLERS WITH TRANSPORT CAP

(75) Inventor: Robert Zeller, Kempten (DE)

(73) Assignee: Endress + Hauser Wetzer GmbH + Co. KG, Nesselwang (DE)

( * ) Notice: Subject to any disclaimer, the term of this patent is extended or adjusted under 35 U.S.C. 154(b) by 997 days.

(21) Appl. No.: 10/308,181

(22) Filed: Dec. 3, 2002

(65) Prior Publication Data

US 2003/0136700 A1     Jul. 24, 2003

Related U.S. Application Data

(60) Provisional application No. 60/334,582, filed on Dec. 3, 2001.

(51) Int. Cl.
*B65B 3/00*     (2006.01)
*G01N 1/14*    (2006.01)

(52) U.S. Cl. .................. 141/284; 141/130; 73/863; 73/863.83

(58) Field of Classification Search .............. 141/284, 141/130; 73/863, 863.83, 864.34, 863.01; 222/14
See application file for complete search history.

(56) References Cited

U.S. PATENT DOCUMENTS

| 3,838,719 | A | * | 10/1974 | Lederer ...................... 141/284 |
| 4,415,011 | A | * | 11/1983 | Grant ......................... 141/284 |
| 5,546,818 | A | * | 8/1996 | Keefer ......................... 73/863 |
| 5,576,503 | A | * | 11/1996 | Nabity et al. ................. 73/863 |
| 5,726,360 | A | * | 3/1998 | Keefer ......................... 73/863 |
| 6,354,345 | B1 | * | 3/2002 | Nabity et al. ............... 141/284 |

* cited by examiner

*Primary Examiner*—Bryon P Gehman
(74) *Attorney, Agent, or Firm*—Bacon & Thomas, PLLC

(57) ABSTRACT

The container carrier serves to hold containers for fluid samples. For the transport of the sample containers, the container carrier, which is directly but detachably connected with a cover part during the dispensation of fluid samples into the sample containers, is separated from the cover part, with the sample containers remaining in the container carrier in transport. A transport cap is provided for closing the container carrier in transport, particularly in a fluid-tight manner.

18 Claims, 5 Drawing Sheets

CONTAINER CARRIER FOR SAMPLERS WITH TRANSPORT CAP

CROSS REFERENCE TO RELATED APPLICATION

This application is based on Provisional Application No. 60/334,582 filed on Dec. 3, 2001.

TECHNICAL FIELD

This invention relates to a container for holding sample containers serving to receive fluid samples which is suitable for a sampler, particularly for a transportable sampler.

BACKGROUND OF THE INVENTION

To monitor aqueous fluids, particularly in drinking water treatment or sewage treatment plants, representative fluid samples frequently have to be drawn at remote locations and transferred to a laboratory for analysis.

The drawing and transport of such fluid samples are typically carried out automatically by means of samplers installed in situ, which may be portable. Such samplers for preferably automatically taking fluid samples are disclosed, for example, in U.S. Pat. No. 4,415,011, WO-A 9502176, or in applicant's European Patent Application 00 12 2411.2, which was not published prior to the filing date of the present application. Each of those samplers comprises a container carrier for holding sample containers for receiving fluid samples and a cover part for closing the container carrier.

Furthermore, the samplers each comprise a pumping device disposed within the sampler housing for drawing fluid from a source of fluid and for filling fluid samples into the sample containers, as well as control electronics, which are also contained in the sampler housing.

To transport the sample containers from the sampler to the laboratory, use is generally made of a separate, particularly basket-like, sample container holder which, as described in WO-A 9502176, for example, can also be used as an insert for the container carrier. It is also common practice to bring transportable, particularly portable, samplers to the laboratory in toto.

A disadvantage of the first-mentioned transport variant is that, aside from the additional component for the sampler, namely the sample container holder, an additional transport container is necessary to isolate the sample containers from perturbing environmental influences and, if necessary, protect them against unauthorized access. In the other of the two aforementioned transport variants, the main disadvantage lies in the fact that the sampler may have to be installed several times at the same sample-gathering location merely for transport reasons.

SUMMARY OF THE INVENTION

Starting from the above-described disadvantages of conventional samplers, an object of the invention is to improve the transport of the container carriers so that, particularly without adding a major amount of technical complexity and particularly by using existing sampler concepts, both simple and convenient transport and virtually continuous operation of the sampler are made possible.

To attain this object, the invention provides a container carrier for holding sample containers for receiving fluid samples which during the dispensation of fluid samples into sample containers held therein is directly and detachably connected with a cover part of a sampler, and which for the transport of sample containers held therein is separated from the sampler, with the sample containers remaining in the container carrier in transport.

In a first preferred embodiment of the invention, during the transport of sample containers, the container carrier is closed with a detachably fixed transport cap.

In a second preferred embodiment of the invention, the container carrier is closed with the transport cap in a fluid-tight manner.

In a third preferred embodiment of the invention, during the dispensation of fluid samples, the container carrier is detachably connected with a transportable, particularly portable, sampler.

One advantage of the invention lies in the fact that the sampler can be easily made ready for immediate reuse, e.g., by providing it with a further container carrier that has already been equipped with suitable sample containers.

The invention and further advantages will become more apparent from the following description of embodiments taken in conjunction with the accompanying drawings. Throughout the various figures of the drawings, like parts are designated by like reference characters; reference characters that have already been assigned are not repeated in subsequent figures if this contributes to clarity. In the drawings:

DESCRIPTION OF THE PREFERRED EMBODIMENTS

Figure 1:
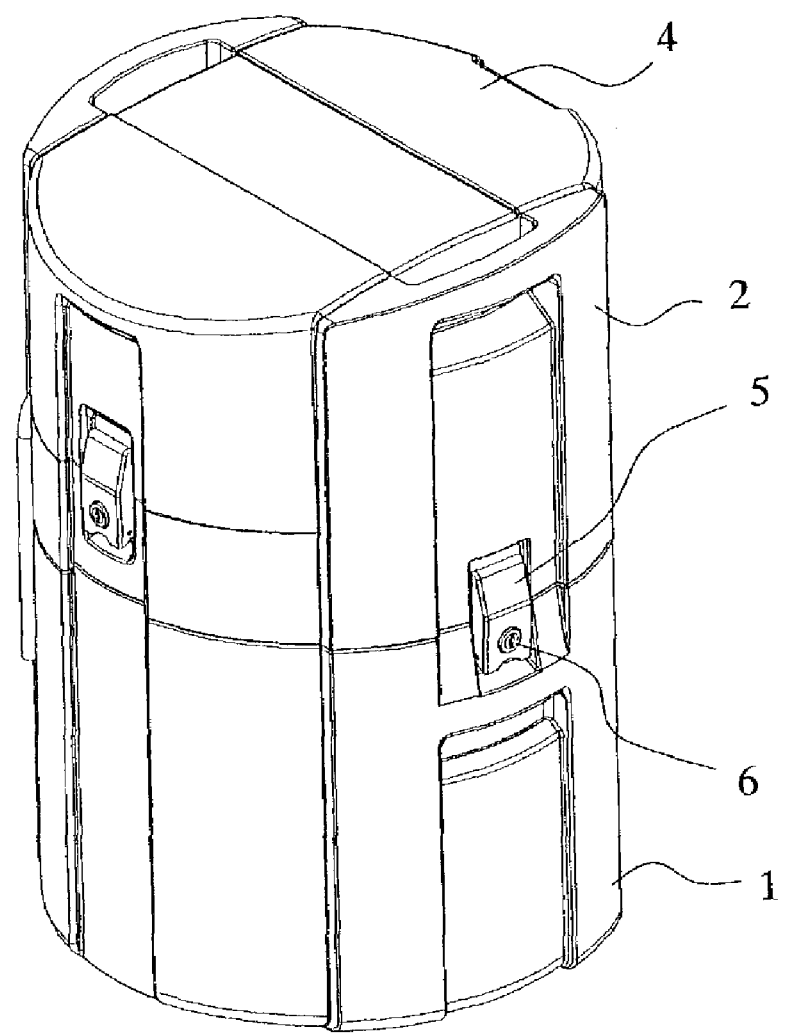
FIG. 1 is a perspective view of a sampler with a container carrier and a cover part.
Figure 2:
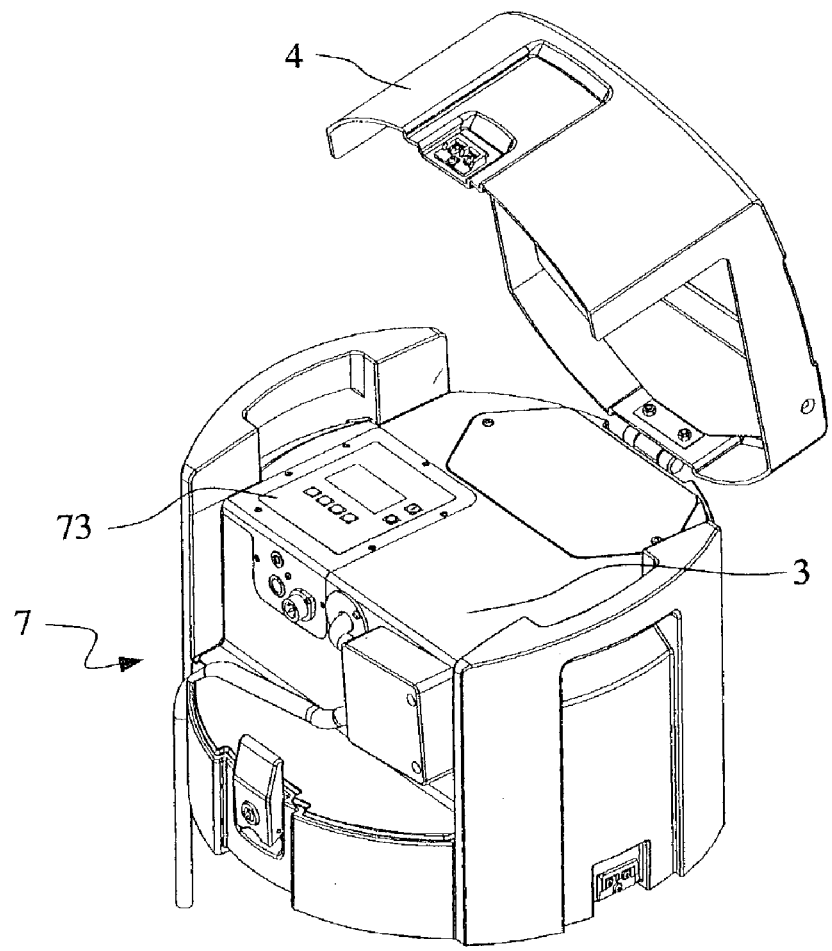
FIG. 2 is a first exploded view of the sampler of FIG. 1.
Figure 2:
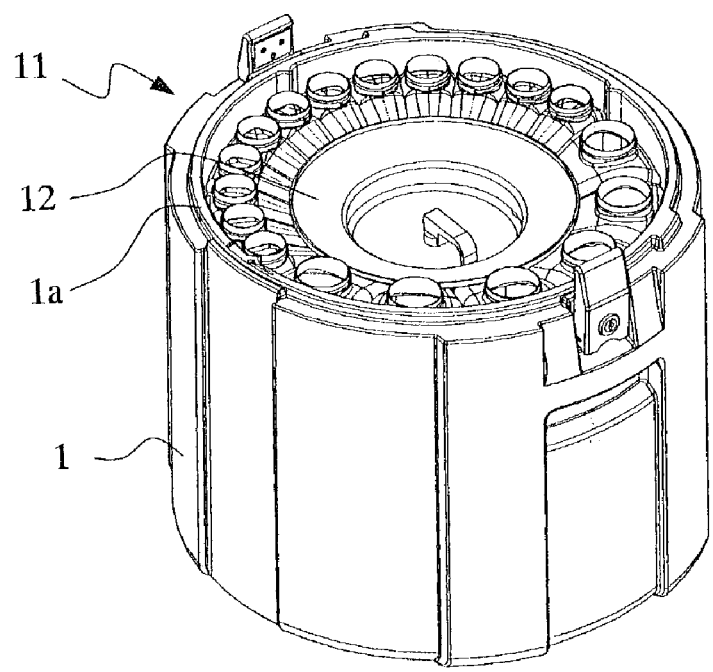
Figure 3:
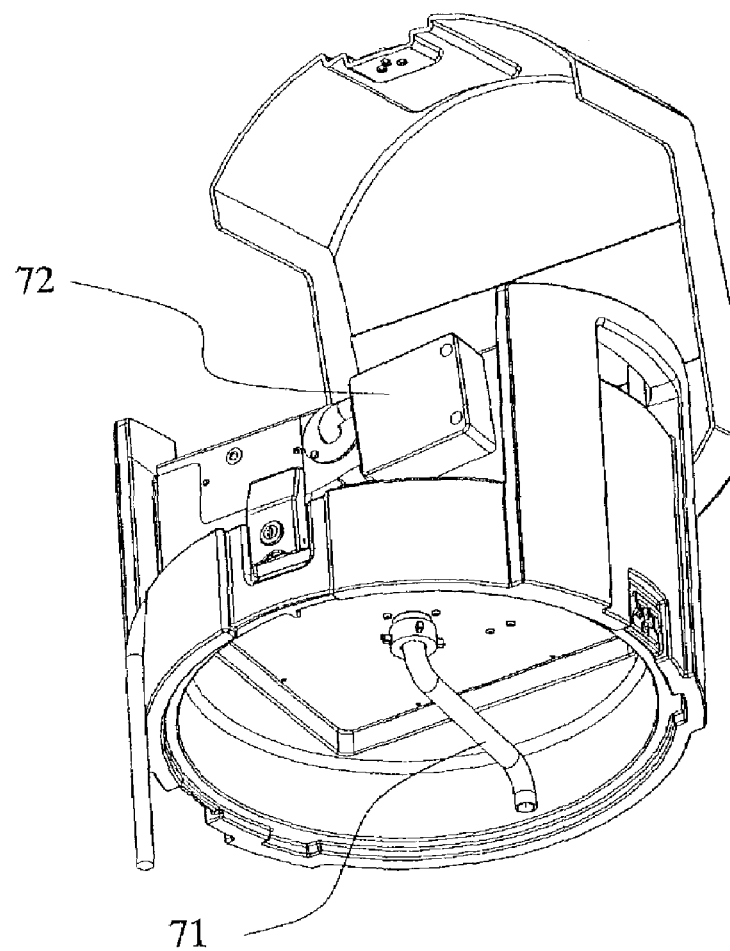
FIG. 3 is a second exploded view of the sampler of FIG. 1.
Figure 3:
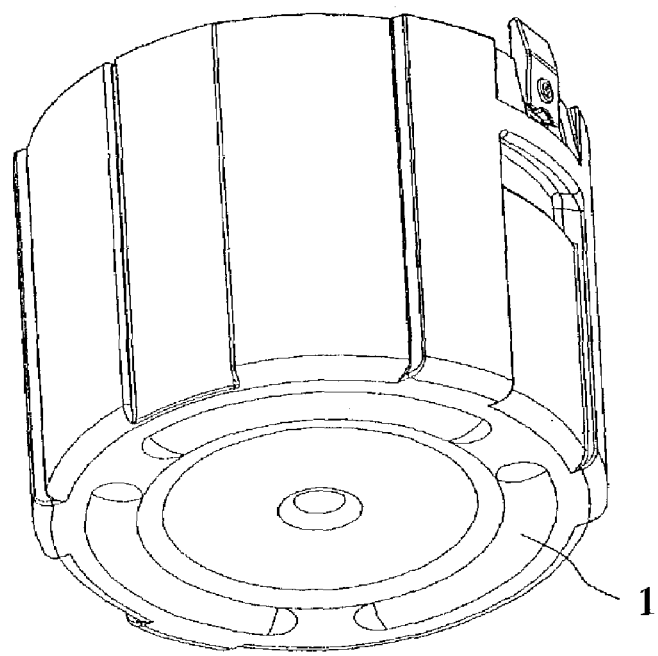

FIGS. 1, 2, and 3 show schematically an embodiment of a transportable, particularly portable, sampler with a lockable housing. The sampler serves to draw samples of dunking water or wastewater, for example.

The housing of the sampler is formed by a pot- or bucket-shaped container carrier 1 for holding sample containers 11, and by a cover part 2. For the dispensation of fluid samples into one or more of the sample containers 11, container carrier 1 is closed with a cover part 2, particularly in a liquid-tight manner. Container carrier 1 and cover part 2 are preferably made of plastic, e.g., polyethylene, and can be manufactured in the manner familiar to those skilled in the art, e.g., by rotational casting or injection molding.

As is usual with such samplers, the sample containers 11 are preferably arranged within container carrier 1 in a ring, such that, at least with the carrier closed by cover part 2, this ring is concentric with a, particularly rotatable, sample distributor 71 of a pumping device 7 of the sampler. To fix the sample containers 11 in container carrier 1, use is preferably made of a suitable, here plate-shaped, hold-down 12 which presses against the sample containers 11 so as to hold them firmly in position.

The sample distributor 71 is rotatably mounted to cover part 2 and serves to fill sample containers with fluid samples taken in operation by means of a pump 72 of the sampler, e.g., a peristaltic pump. As a drive for rotating the sample distributor 71, a stepper motor, for example, may be used.

Cover part 2 preferably incorporates an electronics case 3 which houses control electronics (not shown), e.g., electronics for controlling the pumping device 7, and, being preferably liquid-tight, protects the control electronics from external influences. Electronics case 3 may also be mounted on cover part 2 as a separate component, of course. Furthermore, the aforementioned stepper motor may also be housed in electronics case 3, and/or pump 72 may be fixed to electronics case 3 from outside.

Also mounted in cover part 2 is an input/output unit 73 which is connected to the control electronics and serves to manually enter control signals and/or visually output measured or operating data. As shown in FIGS. 2 and 3, a, particularly lockable, lid 4 may be hinged to cover part 2 for making pump 72 and input/output unit 73 inaccessible.

To laterally locate the cover part 2 in position on container carrier 1, a lip 1a is formed on an upper edge of container carrier 1 along a cross-sectional line, such that it projects into the interior of the put-on cover part 2 and is at least partly in contact with the latter.

Figure 4:
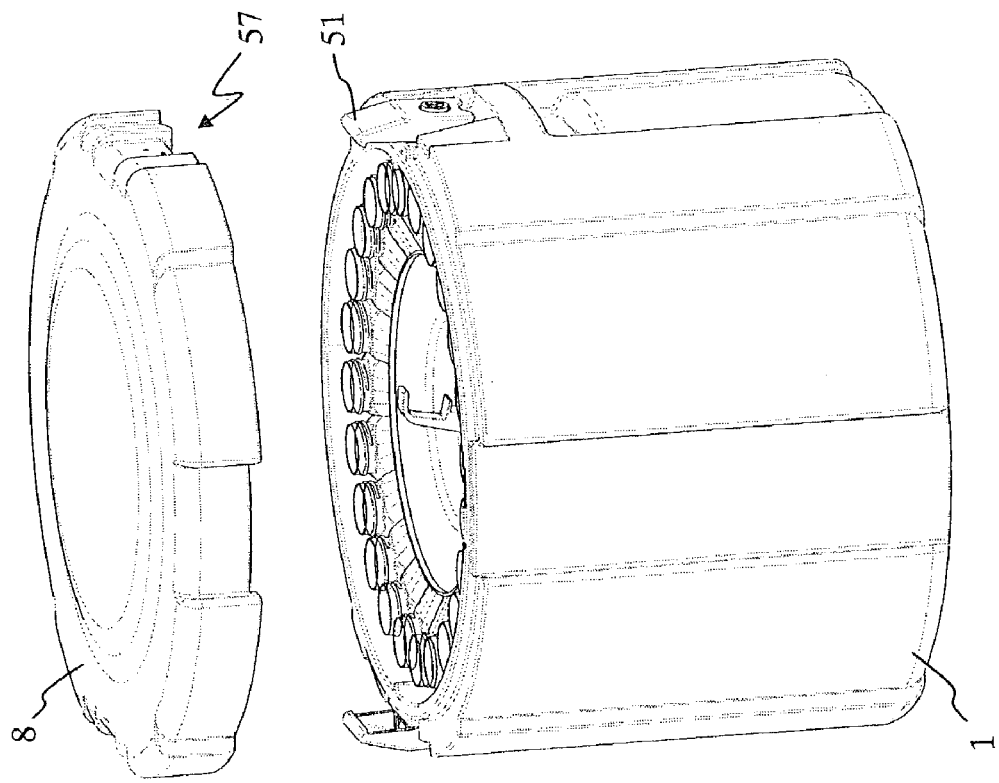
FIG. 4 is a perspective view of the container carrier of FIG. 1, separated from the cover part.

Besides holding the sample containers 11 during the filling operation, according to the invention, container carrier 1 is also designed to hold the sample containers 11 during transport to, e.g., a remote laboratory. In other words, for the purpose of transport, a functional unit formed by container carrier 1, sample containers 11 and, if present, hold-down 12 for the dispensation of fluid samples will be detached from cover part 2, as will be readily apparent when FIGS. 1, 2, and 4 are viewed together, and will remain united during the transport of the fluid samples.

To permit the transport of sample containers 11 in container carrier 1, cover part 2 is completely removable from container carrier 1, as shown in FIGS. 2 and 3.

Figure 5:
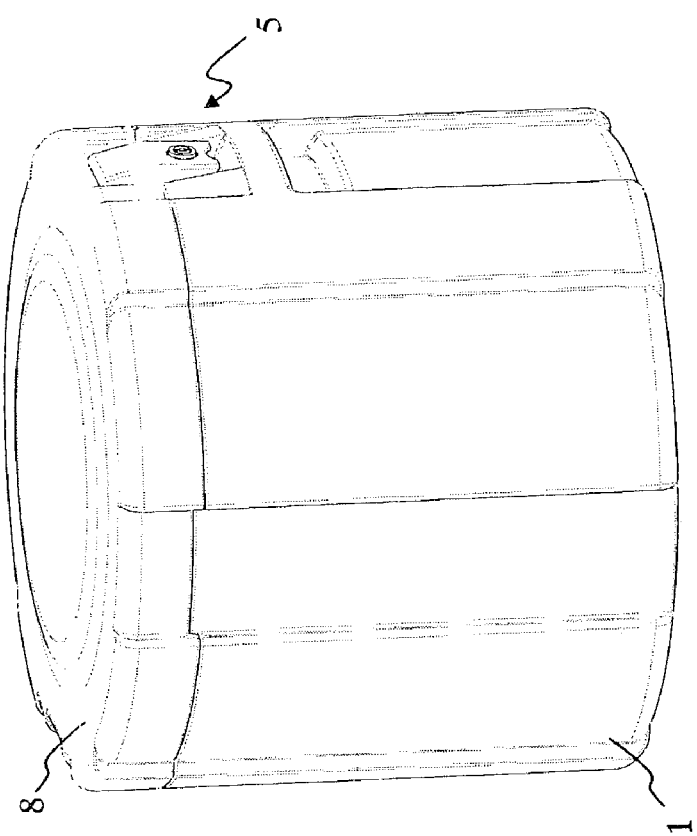
FIG. 5 is a perspective view of the container carrier of FIG. 1, closed with a transport cap.

In a preferred embodiment of the invention, during the transport of sample containers 11 held therein, container carrier 1, as shown in FIG. 5, is covered with a detachably fixed transport cap 8, particularly in a liquid- or even gas-tight manner. Transport cap 8 is preferably made of the same material as container carrier 1 or cover part 2.

One advantage of the use of transport cap 8 is that the sample containers 11 can be protected both from perturbing environmental influences and, as will be explained below, in a simple manner from unauthorized access.

To detachably fix the cover part 2 or the transport cap 8 to container carrier 1, at least one clamp lever latch 5 is provided, as shown in FIGS. 1 to 5.

If necessary, the sampler housing may comprise two clamp lever latches, as shown in FIG. 2. Such clamp lever latches, as is well known, serve to convert a pressure force exerted, particularly manually, on a clamp lever to a tensile force which clasps two components that are movable against each other. Instead of the clamp lever latch 5, other clamp lever latches familiar to those skilled in the art, particularly a latch functioning in the manner of a ski boot fastening, may be employed.

Figure 6:
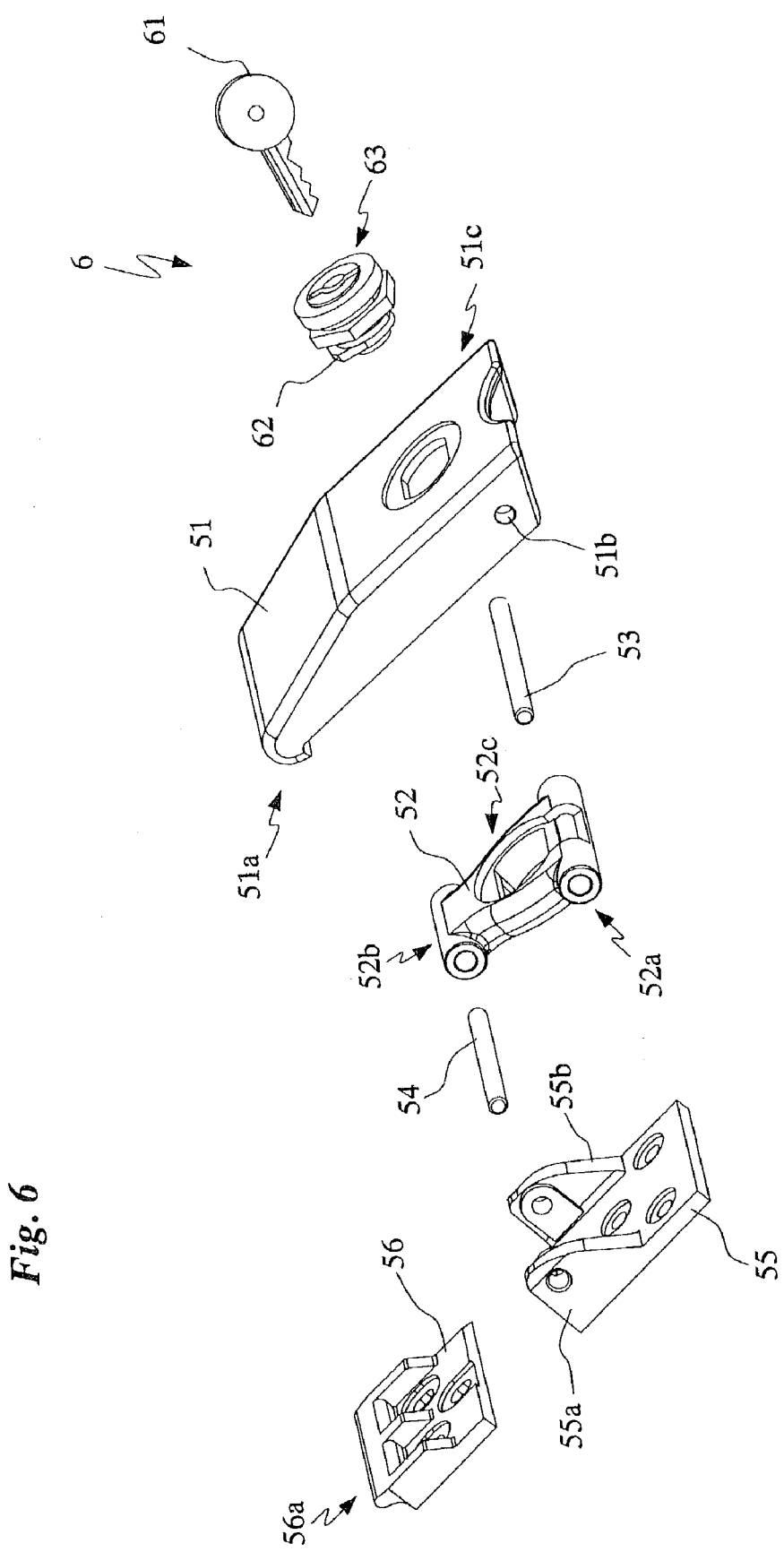
FIG. 6 is an exploded view of a clamp lever latch of the sampler housing of FIG. 1.

In another preferred embodiment of the invention, the clamp lever latch 5, as shown schematically in FIG. 6, has a, particularly rigid, clamp lever 51 which is pivoted to a supporting element 52 at a first end and has a barb 51a formed on a second end. When the clamp lever latch 5 is closed, barb 51a is hooked either in a first clevis-type element 56 of clamp lever latch 5, which is attached to cover part 2, or in an essentially identically shaped second clevis-type element 57 of the latch, which is attached to transport cap 8, and forced against this clevis-type element 56, 57, which serves as an abutment, as is readily apparent from FIGS. 1, 2, and 6 or from FIG. 4.

To rotatably connect clamp lever 51 and supporting element 52, the latter has at a first end a first bearing 52a, which receives a first journal pin 53 of clamp lever latch 5, such that the two ends of this pin protrude laterally from bearing 52a. At a second end, supporting element 52 has a second bearing 52b, which is essentially parallel to bearing 52a and receives a second journal pin 54 of clamp lever latch 5 such that the two ends of this pin protrude laterally from bearing 52b.

To fix journal pin 53 in bearing 52a, the first end of clamp lever 51 has two holes 51b, 51c which are so aligned relative to each other that the axial pin fixed therein is essentially parallel to barb 51a (hole 51c is concealed in FIG. 6).

As shown in FIG. 2, clamp lever 51 is preferably hinged to container carrier 1; if necessary, it may also be mounted to cover part 2.

To mount clamp lever 51 to container carrier 1 or cover part 2, clamp lever latch 5 comprises a mounting plate 55 with a first and a second shoulder 55a, 55b formed thereon. Shoulders 55a, 55b have respective holes for receiving the journal pin 54 located in bearing 52b of supporting element 52. Shoulders 55a, 55b are shaped so that with clamp lever latch 5 closed, the hooked-in clamp lever 51 with the supporting element 52 hinged thereto is stabilized in an end position through elastic prestresses.

As indicated in FIG. 2, mounting plate 55 is fixed in the vicinity of the upper edge of container carrier 1, e.g., by means of screws or rivets.

Opposite mounting plate 55, clevis-type element 56 is attached to cover part 2, such that, on the one hand, a nose 56a formed on clevis-type element 56 and serving to hook in the clamp lever 51 is essentially parallel to barb 51a. On the other hand, clevis-type element 56 and mounting plate 55 are spaced such a distance apart that with clamp lever 51 hooked in, clamp lever latch 5 can overcome an upper dead-center position of maximum tension and that in the closed clamp lever latch 5, a prestressing force will become effective such that cover part 2 and container carrier 1 will be pressed against each other and thus held together. The prestressing force may be so great that clamp lever latch 5, container carrier 1, and/or cover part 2 will be slightly elastically deformed. To secure clevis-type element 56 to cover part 2, screw or rivet joints, for example, may be used. In a manner analogous to that of clevis-type element 56, clevis-type element 57 is attached to transport cap 8.

Suitable materials for clamp lever 51, supporting element 52, mounting plate 55, and/or clevis-type elements 56, 57 are plastics or metal alloys, for example.

In a further preferred embodiment, clamp lever latch is lockable, 6, so that container carrier 1, covered with cover part 2 or transport cap 8, is protected against unauthorized or unintentional opening, cf. the above-mentioned European Patent Application 00 12 2411.2.

The invention claimed is:

1. A sampler for drawing samples of a fluid, said sampler comprising:
a container carrier holding sample containers therein;
a cover part detachably connected with said container carrier during drawing of samples of fluid, a sample distributor for filling a sample container with a fluid sample, said sample distributor being mounted to the cover part; and a transport cap detachably connectable with said container carrier if said cover part is detached from said container carrier.

2. The sampler as claimed in claim 1, wherein:

said cover part is detached from said container carrier during transportation of said sample containers held within said container carrier.

3. The sampler as claimed in claim 1, wherein:

said transport cap is connected with said container carrier during transportation of said sample containers held within said container carrier.

4. The sampler as claimed in claim 3 wherein:

said container carrier is closed with said transport cap in a fluid-tight manner.

5. The sampler as claimed in claim 3, further comprising:

a pump for taking fluid samples; and control electronics for controlling said sample distributor and said pump, wherein:

said control electronics are incorporated in said cover part.

6. The sampler as claimed in claim 3, further comprising:

a pump mounted to said cover part.

7. The sampler as claimed in claim 6, further comprising:

control electronics for controlling said pump, wherein:

said control electronics are incorporated in said cover part.

8. The sampler as claimed in claim 3, further comprising:

a stepper motor for driving said sample distributor.

9. The sampler as claimed in claim 8, further comprising:

control electronics for controlling said stepper motor, wherein:

said control electronics are incorporated in said cover part.

10. The sampler as claimed in claim 3 further comprising:

clamp lever latches for detachably connecting said cover part with said container carrier and for detachably connecting said transport cap with said container carrier, respectively.

11. The sampler as claimed in claim 10 wherein:

at least one of said clamp lever latches is lockable.

12. The sampler as claimed in claim 1, further comprising:

a pump for taking fluid samples; and control electronics for controlling said sample distributor and said pump, wherein:

said control electronics are incorporated in said cover part.

13. The sampler as claimed in claim 1, further comprising:

a pump mounted to said cover part.

14. The sampler as claimed in claim 13, further comprising:

control electronics for controlling said pump, wherein:

said control electronics are incorporated in said cover part.

15. The sampler as claimed in claim 1, further comprising:

a stepper motor for driving said sample distributor.

16. The sampler as claimed in claim 15, further comprising:

control electronics for controlling said stepper motor, wherein:

said control electronics are incorporated in said cover part.

17. The sampler as claimed in claim 1 further comprising:

clamp lever latches for detachably connecting said cover part with said container carrier and for detachably connecting said transport cap with said container carrier, respectively.

18. The sampler as claimed in claim 17 wherein:

at least one of said clamp lever latches is lockable.

* * * * *